United States Patent [19]
Garrity et al.

[11] Patent Number: 5,958,373
[45] Date of Patent: Sep. 28, 1999

[54] POLYCHELANTS AS CONTRAST ENHANCING AGENTS

[75] Inventors: Martha Garrity, San Clemente; Shaun Paul Crofts, Campbell; Joan Carvalho, Mountain View, all of Calif.; Per Strande; Harald Dugstad, both of Oslo, Norway

[73] Assignee: Nycomed Salutar Inc., Wayne, Pa.

[21] Appl. No.: 08/615,241

[22] PCT Filed: Sep. 6, 1994

[86] PCT No.: PCT/GB94/01931

§ 371 Date: Jun. 13, 1996

§ 102(e) Date: Jun. 13, 1996

[87] PCT Pub. No.: WO95/07270

PCT Pub. Date: Mar. 16, 1995

[30] Foreign Application Priority Data

Sep. 7, 1993 [GB] United Kingdom .................... 9318550

[51] Int. Cl.$^6$ ............................ A61B 5/055; A61K 49/04
[52] U.S. Cl. .................... 424/1.65; 424/9.363; 424/9.42; 514/184; 514/836; 540/465
[58] Field of Search ................ 424/1.65, 9.363, 424/9.42; 534/15, 16; 436/173; 600/420; 514/184, 836; 540/465

[56] References Cited

U.S. PATENT DOCUMENTS

| | | | |
|---|---|---|---|
| 5,049,667 | 9/1991 | Schaefer et al. | 540/474 |
| 5,394,416 | 2/1995 | Rousseaux et al. | 424/2 |
| 5,446,145 | 8/1995 | Love et al. | 540/465 |
| 5,645,818 | 7/1997 | Jackels et al. | 424/9.363 |
| 5,650,133 | 7/1997 | Carvalho et al. | 424/1.65 |

FOREIGN PATENT DOCUMENTS

| | | |
|---|---|---|
| 0 255 471 A1 | 2/1988 | European Pat. Off. |
| 0 485 045 A2 | 5/1992 | European Pat. Off. |
| WO 91/05762 | 5/1991 | WIPO |
| WO 92/16494 | 10/1992 | WIPO |
| WO 93/12096 | 6/1993 | WIPO |

*Primary Examiner*—Gary E. Hollinden
*Attorney, Agent, or Firm*—Fish & Richardson P.C.

[57] ABSTRACT

The present invention provides a polychelant compound of formula (VII), (wherein each X which may be the same or different is NZ, O or S, at least two Xs being NZ; B is ($CR^1Y$) or —$N(CR^1_2Y)$—; each Z is a group $R^1$ or a group $CR^1_2Y$, at least one Z being a group $CR^1_2Y$; each Y is a group $CO_2H$, $PO_3H$, $SO_3H$, $CONR^1_2$, $CON(OR^1)R^1$, CNS or $CONR^1NR^1_2$; m is 0 or 1 or 2; each n is 2 or 3; q is 0 or 1 when B is ($CR^1Y$) and 2 when B is $N(CR^1_2Y)$; p is an integer having a value of at least 2; each $R^1$ which may be the same or different is a hydrogen atom or an alkyl, aryl or aralkyl group optionally substituted by one or more hydroxy or alkoxy groups, or two $R^1$ groups on ring atoms or in Z groups together represent a linker group L; each L which may be the same or different represents a bond or an organic linker group having a molecular weight of less than 1000 and salts and chelates thereof. These compounds, especially the diand trichelates with paramagnetic or heavy metal ions are especially useful as diagnostic imaging contrast agents.

21 Claims, No Drawings

POLYCHELANTS AS CONTRAST ENHANCING AGENTS

The present invention relates to chelating agents capable of complexing more than one metal ion simultaneously, especially oligochelants, and more particularly dichelants, and to chelates and salts thereof and their use in diagnostic and therapeutic compositions, especially as contrast enhancing agents in diagnostic medical imaging.

The medical use of chelants is now well established, for example as stabilisers for pharmaceutical preparations, as antidotes for poisonous heavy metal species, as carriers for diagnostically or therapeutically useful metal ions, for example in contrast media for use in magnetic resonance, X-ray or ultrasound imaging or in scintigraphy.

For such diagnostic agents, it is generally important that the chelate complexes should be stable both kinetically and thermodynamically and for this reason there has been much interest in the macrocyclic polyamine-based chelates, in particular DOTA and its derivatives and analogues, which form very stable complexes with the lanthanide metal ions such as gadolinium and dysprosium which are favoured diagnostic metal ions for magnetic resonance imaging due to their relatively large effects on the relaxation times (e.g. $T_1$ and $T_2^*$) of neighbouring water protons.

The paramagnetic lanthanide metal ions useful as MR imaging contrast agents are relatively toxic and for clinical use must be administered in a form which allows little or no release of the metal for subsequent biological uptake and retention. For this reason, from the early years of MR contrast agents, the use of stable chelate complexes has been proposed. Thus the first commercial lanthanide based MR imaging contrast agent, Magnevist, contained GdDTPA, a complex with a high stability constant which following parenteral administration is excreted relatively rapidly by glomerular filtration with the gadolinium still in the chelate complex.

GdDOTA has an even higher reported $pK_{ML}$ and thus was also a prime candidate for consideration as an MR imaging contrast agent. DOTA (1,4,7,10-tetraazacyclododecane-N,N',N'',N'''-tetraacetic acid) and HPDO3A (1-(2-hydroxypropyl)-4,7,10-tetraazacyclododecane-N,N',N''-triacetic acid) have indeed been proposed as chelants for MR imaging contrast agents and GdDOTA and GdHPDO3A have been the subject of extensive human clinical trials by companies active in this field.

The lanthanide metals generally have a stable +3 oxidation state and DOTA with its four carboxylic acid groups results in a charged complex, i.e. GdDOTA⁻, requiring a counterion. Analogous uncharged complexes may be produced by eliminating one of DOTA's nitrogen-attached carboxymethyl groups or by replacing it with a non-ionizing group, i.e. by using a chelant such as DO3A (1,4,7,10-tetraazacyclododecane-N,N',N''-triacetic acid) or HPDO3A.

Contrast media based on such non-ionic, or overall charge neutral, complexes have lower osmolalities for a given metal ion concentration and can demonstrate other improved properties relative to the analogous charged complexes. Moreover, the ring nitrogen "freed" by removal of the carboxymethyl group in moving from DOTA to DO3A can of course be substituted by groups which can act to enhance the hydrophilicity or lipophilicity or other biodistribution affecting properties of the chelate.

Recently, there has been growing interest in the use of chelants capable of chelating more than one metal ion per chelant molecule as carriers for paramagnetic or heavy metal ions for MR or X-ray imaging contrast agents. These polychelants offer several advantages over the monochelants such as DTPA, DO3A or DOTA. Thus for example, the osmolality at a given metal concentration can be reduced still further, the simultaneous delivery of a plurality of metal ions to a target site can be facilitated, and more efficient contrast agents can be produced.

Polychelants range from dichelants through oligochelants to true polychelants having perhaps hundreds of chelant moieties per molecule. Many such compounds have been described but there is still a need for polychelants, and in particular oligochelants and especially dichelants, having improved properties in terms for example of relaxivity, stability, biodistribution, biotolerability, viscosity, solubility and osmolality.

Particular macrocyclic dichelants described in the literature include the DO3A dimers of formula I, II, III and IV whose preparation has been described by Nycomed Salutar Inc. in WO-A-91/05762 and by Schering AG in EP-A-255471 and EP-A-485045 and elsewhere.

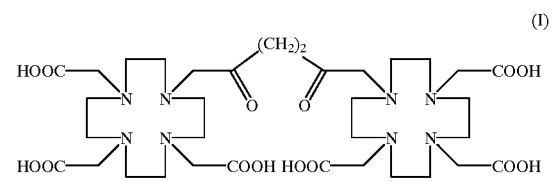

(I)

(described by Salutar in WO-A-91/05762)

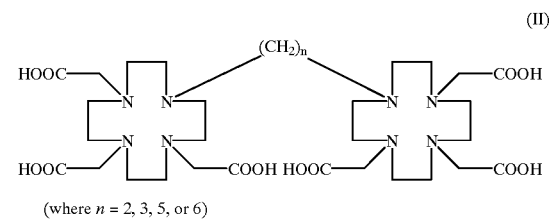

(II)

(where $n$ = 2, 3, 5, or 6)

(described by Schering AG in EP-A-255471 and in a poster presented at the ninth annual SMRM meeting in New York, Aug. 18 to 24, 1990)

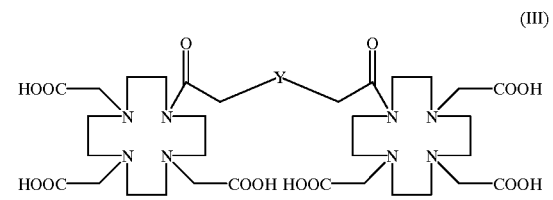

(III)

(where Y is [—N(CH₂COOH)CH₂CH₂N(CH₂COOH)CH₂CH₂N(CH₂COOH)]ₐ and a=0 or 1)

(described by Schering AG in EP-A-255471)

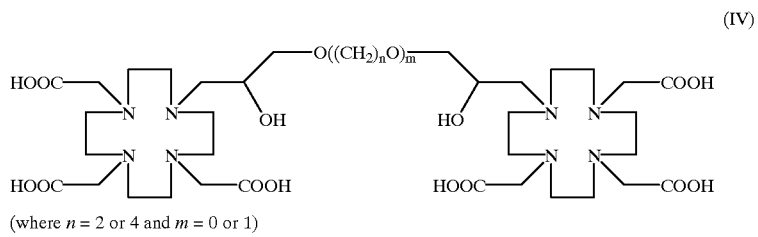

(where $n = 2$ or $4$ and $m = 0$ or $1$)

(described by Schering AG in EP-A-485045).

All of these prior art macrocyclic chelant dimers have the general formula DO3A'-L-DO3A' where DO3A' is a ring nitrogen deprotonated DO3A residue and L is a linker group.

With lanthanides such as gadolinium, these macrocyclic dimers will produce non-ionic dichelates and these compounds have been found to possess high relaxivity. Thus for example the T1 relaxivities of the bisgadolinium chelates of the compounds of formula II are almost double the T1 relaxivity of GdDO3A.

We now propose however that macrocyclic dimers (and oligomers) be produced by using the linker moiety to connect not to a vacant ring nitrogen but to an alkyl support of one of the chelating groups (e.g. in DO3A to the methylene group of one of the three nitrogen-attached carboxymethyl groups). In this way the free ring nitrogen is left available for substitution by biodistribution-modifying substituents as in the monochelant DO3A itself. At its simplest, the resultant macrocyclic dimer would have the structure

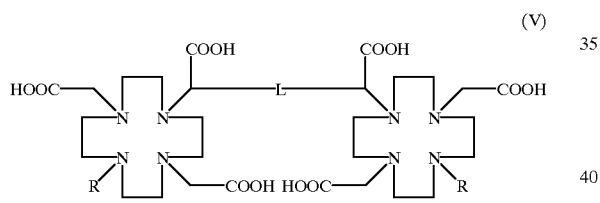

where R is hydrogen or a distribution modifying substituent and L is a linker group.

Where linker L is short, the macrocyclic dimer is relatively rigid leading to improved $T_1$ relativity. This can also be achieved by using two such linker groups attached to the alkyl structure of adjacent chelating groups. At its simplest, a compound of this nature would therefore have the structure:

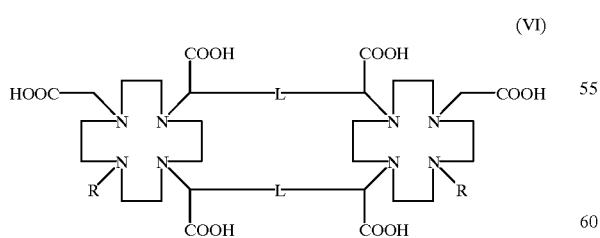

Finally, the concept of linking macrocyclic chelants at the alkyl support of one of the ring attached chelating moieties is applicable generally to oligochelants as well as to dichelants. Viewed from one aspect therefore the present invention provides a polychelant of formula VII

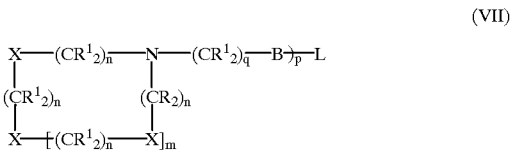

(wherein each X which may be the same or different is NZ, O or S, at least two Xs being NZ;

B is $(CR^1Y)$ or $-N(CR^1{}_2Y)-$;

each Z is a group $R^1$ or a group $CR^1{}_2Y$, at least one Z being a group $CR^1{}_2Y$;

each Y is a group $CO_2H$, $PO_3H$, $SO_3H$, $CONR^1{}_2$, $CON(OR^1)R^1$, CNS or $CONR^1NR^1{}_2$, preferably COOH;

m is 0 or 1 or 2, preferably 1; each n is 2 or 3; q is 0 or 1 when B is $(CR^1Y)$ and 2 when B is $N(CR^1{}_2Y)$;

p is an integer having a value of at least 2;

each $R^1$ which may be the same or different is a hydrogen atom or an alkyl, aryl or aralkyl group optionally substituted by one or more hydroxy or alkoxy groups, or two $R^1$ groups on ring atoms or in Z groups together represent a linker group L;

each L which may be the same or different represents a bond or an organic linker group having a molecular weight of less than 1000) and salts and chelates thereof.

In the compounds of the invention, the macrocyclic

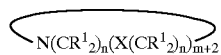

rings preferably have 9 to 14 ring atoms, the ring heteroatoms especially preferably being either all nitrogen or being one oxygen and three nitrogens. The alkylene ring segments $(CR^1{}_2)_n$ preferably are all $(CR^1{}_2)_2$ groups or in the case of an $N_4$ macrocycle the alkylene segments may alternatively be alternating $(CR^1{}_2)_3$ and $(CR^1{}_2)_2$ groups. Thus the preferred macrocyclic skeletons are those of formulae VIII

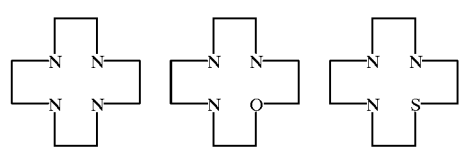

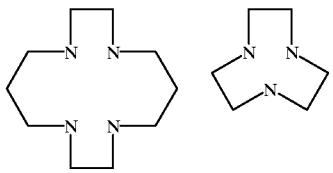

Preferably none, 1, 2 or 3, especially none, of the macrocyclic ring carbons are substituted, and indeed in general $CR^1_2$ moieites are preferably $CH_2$ groups.

The linker groups L will preferably be linear, branched or cyclic alkylene groups or combinations thereof or arylene groups or combinations of arylene and alkylene groups, for example providing a linking backbone 1 to 50 atoms long but preferably 2 to 10, and especially 2 to 5 atoms long in total on any one unbranched segment. The carbon backbone in such linker groups may be interrupted by heteroatoms such as nitrogen, oxygen, sulphur, boron and phosphorus, and may carry bridging groups, thereby creating homo- or heterocyclic rings within the linker moiety. Where this occurs, the rings created will preferably be 3 to 12, especially 5 to 8 and particularly 6, membered. Moreover the rings and the linear segments of the linker moiety may optionally be unsaturated and may optionally carry one or more substituents selected from oxo, alkyl, hydroxy, alkoxy, amine, aryl and substituted aryl groups as well as non-hydrogen $R^1$ groups or additional chelating groups, eg. Y groups especially carboxyl and $SO_3H$ groups, and groups such as for example long chain (eg. $C_{10-20}$) alkyl, aryl or polyaryl groups which are suitable for liposomal incorporation of the compound of formula VII or groups, such as isothiocyanate groups, for attachment of the compound of formula VII to a biomolecule, polymer, dendrimer or other macromolecule, for example to create a polychelant or a bifunctional chelant.

The linker moiety of the compounds of the invention may, as indicated above, each serve to link together two or more chelant moieites, thereby holding together the di- or polychelate structure. Besides filling this role as linker or spacer of chelant sites, the linker moiety can be so selected as to yield a product having other desired characteristics. For example it is possible to increase hydrophilicity, lipophilicity, or tissue specificity of the end product by attaching to or incorporation within linker moieties groups which are hydrophilic, lipophilic, or tissue targeting. In this way, the overall charge of the chelate structure, or the overall lipophilicity, or tissue targeting can be controlled.

The primary function of linker L however is to link together two or more macrocyclic chelant moieties and its precise chemical nature is of lesser importance as long as this function is fulfilled. Generally however linker gruops which individually or together provide a relatively rigid linkage between the macrocycles are preferred.

In formula VII, p is preferably 2, 3 or 4 and where linker L serves to join together 2, 3 or 4 macrocycles it will preferably have a linking backbone of 1 to 12 atoms, e.g. L may be $CH_2$, $(CH_2)_2$, $(CH_2)_3$, $(CH_2)_4$, $(CH_2)_3CH$, $(CH_2CH_2)_3CH$, $(CH_2CH_2)_4C$, etc. Where only two macrocycles are linked, L will preferably have a backbone of 2 to 4 atoms, and especially preferably is $CH_2CH_2$. Where two $R^1$ groups together form a linker moiety, this will preferably be between Z groups and will also preferably be 2 to 4 atoms in length.

In the compounds of formula VII, alkyl moieties preferably have 1 to 6, especially 1 to 4 carbon atoms unless otherwise specified, and aryl moieties are preferably phenyl groups.

Particularly preferred compounds of formula VII include those of formula IX

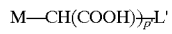

(IX)

where M is a nitrogen attached triaza, tetraaza, triazaoxa or triazathia-cycloalkane of formula VIII having at least one and preferably two ring nitrogens substituted by $CH_2COOH$ groups and having any remaining ring nitrogen substituted by a group $R^2$, M preferably being a group of formula VIII having only one ring heteroatom unsubstituted (ie. an oxygen or sulphur atom) or substituted by a group $R^2$; $R^2$ (which for tetraheteroatom rings is preferably at the ring heteroatom remote from the ring attachment nitrogen) is a hydrogen atom, or an alkyl group optionally mono or polysubstituted by hydroxyl or alkoxy groups (eg. hydroxyalkyl, polyhydroxyalkyl, alkoxyalkyl, polyalkoxyalkyl, hydroxyalkoxyalkyl, polyethylene glycol etc.) and optionally interrupted by arylene or substituted arylene groups; p' is 2, 3 or 4, preferably 2; and L' is a linker group as discussed above, eg. a bond or a saturated or unsaturated alkylene optionally substituted by oxo, amine, hydroxyl, carboxyl, aryl and substituted aryl groups and optionally interrupted by nitrogen, oxygen or sulphur atoms or arylene or substituted arylene groups (eg. CNS substituted to provide a terminal functional group for macromolecule attachment). Particularly preferably M is a 9-substituted 1,4,7,10-tetraazacyclododec-1-yl group and L' is a linker providing a $C_{2-10}$, especially $C_{2-4}$, chain between two M groups.

Especially preferred compounds of formula IX include the dimers of formula X

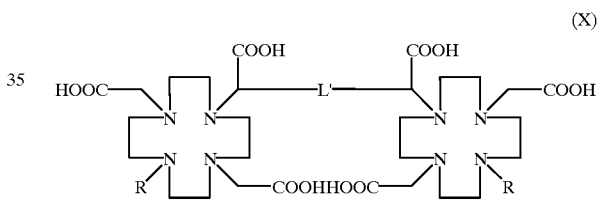

(X)

where L' is —$CH_2CH_2$— and
$R^2$ is 2,3-dihydroxy-1-hydroxymethylpropyl, $CH_3OCH_2CH_2(OCH_2CH_2)_6$—, 5-phenoxy-3-methylpentyl, 1,3-dicarboxypropylamino, or dicarboxyphenylamino or L' is 1-isothiocyanato-3,5-phenylene and $R^2$ is p-sulphophenylethyl, p-ethoxybenzyloxyethyl or $(CH_2)_3N(CH_3)_3Br$, or L' is $(CH_2OCH_2)_t$ where t is 1 to 12 and $R^2$ is 3-phenoxy-2-hydroxypropyl, 11-phenoxy-2-hydroxyundecyl or (2-phenyl-1-carboxyethyl)aminocarbonylmethyl.

Other particularly preferred dimers include those wherein the linker incorporates a negatively or positively charged species, eg. a carboxylate or trimethylammonium group, eg. at the 1-position of a 3,5-phenylene unit of L. These provide the advantage that the $R^2$ groups which can be added during the final stage of synthesis provide a means for dramatically altering the overall lipophilicity or hydrophilicity or charge of the compound's complexes without affecting the metal coordinating groups. The ability to alter these $R^2$ groups offer a way of altering the physicochemical properties (eg. solubility, viscosity, osmolality and relaxivity) and biological properties (eg. biodistribution, toxicity, retention, residence time in blood, organs or elsewhere) of the chelate without affecting the stability of the metal-chelate bond.

The trimers of formula VIII of particular interest include those of formula XI

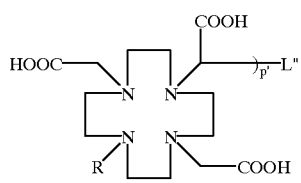

(XI)

where p' is 3 and L" is a group such as

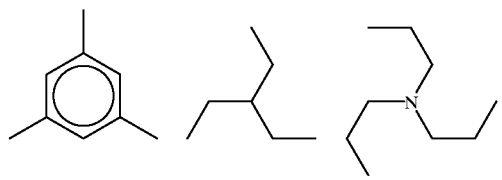

or

or p' is 2 and L" is a linker which incorporates a macrocyclic chelate, eg.

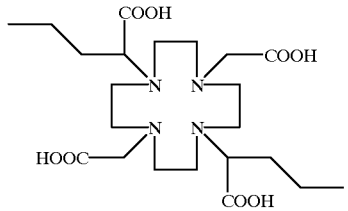

The compounds of the invention may be prepared by conventional synthetic techniques, conveniently starting from the corresponding N-unsubstituted polyazacycloalkanes, condensing these to a polyfunctional linker molecule, generally after protection of one or more of the ring nitrogens, followed by deprotection and introduction of functional groups at the ring nitrogens.

Thus viewed from a further aspect the invention also provides a process for the preparation of the compounds of the invention, said process comprising at least one of the following steps:

(a) reacting a compound of formula VII wherein at least one group X is a group NH, with a compound of formula XII $$Lv\text{—}R^4 \quad (XII)$$

(where Lv is a displaceable leaving group, for example a halogen atom or a substituted sulphonyloxy group, such as chlorine, bromine, iodine, methanesulphonyloxy, phenysulphonyloxy or p-toluenesulphonyloxy groups and $R^4$ is a group $R^1$ other than hydrogen);

(b) reacting a compound of formula XIII

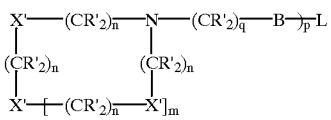

(XIII)

(wherein $R^1$, Y, L, B, p, n, q, and m are as hereinbefore defined, X' is oxygen, NH or $NR^3$, at least one X' being NH, and $R^3$ is hydrogen or a displaceable nitrogen-protecting group) with a compound of formula XIV $$Lv\text{—}CR^1_2Y \quad (XIV)$$

wherein $R^1$, Y and Lv are as defined above;

(c) metallating or transmetallating a compound of formula VII or a chelate thereof;

(d) converting a compound of formula VII or a chelate thereof into a base or acid addition salt thereof or converting a salt into the free acid or base; and (e) performing at least one of steps (a) to (c) above using reagents with protected functional groups and subsequently removing the protecting groups.

The starting compounds of formulae XII and XIV are either known from the literature or can be produced by conventional synthetic techniques. The starting compounds of formula VII used in step (a) can be prepared by the process of step (b). The starting compounds of formula XIII can, as described above, be prepared by condensing the N-unsubstituted macrocycles with polyfunctional linker molecules, for example by reacting a corresponding polybromoalkane derivative with a corresponding $Mo(CO)_3$-protected or borane-protected cyclen.

The most convenient method of preparation is via the coupling of cyclen (using excess cylen to control the reaction) or coupling using a protected cyclen e.g. cyclen orthoformate, or a $MO(CO)_3$ protected or borane protected cyclen or using an appropriate tri-substituted cyclen and the desired bromides. Dibromodicarboxylic acid and dicarboxylic esters such as dibromoadipic acid and dibromosuccinic acid can be purchased from manufacturers or can be prepared by photobromination of the diacid such as dibromoglutaric acid which may be converted to the ester.

By way of Example, the following reaction scheme may thus be utilized:

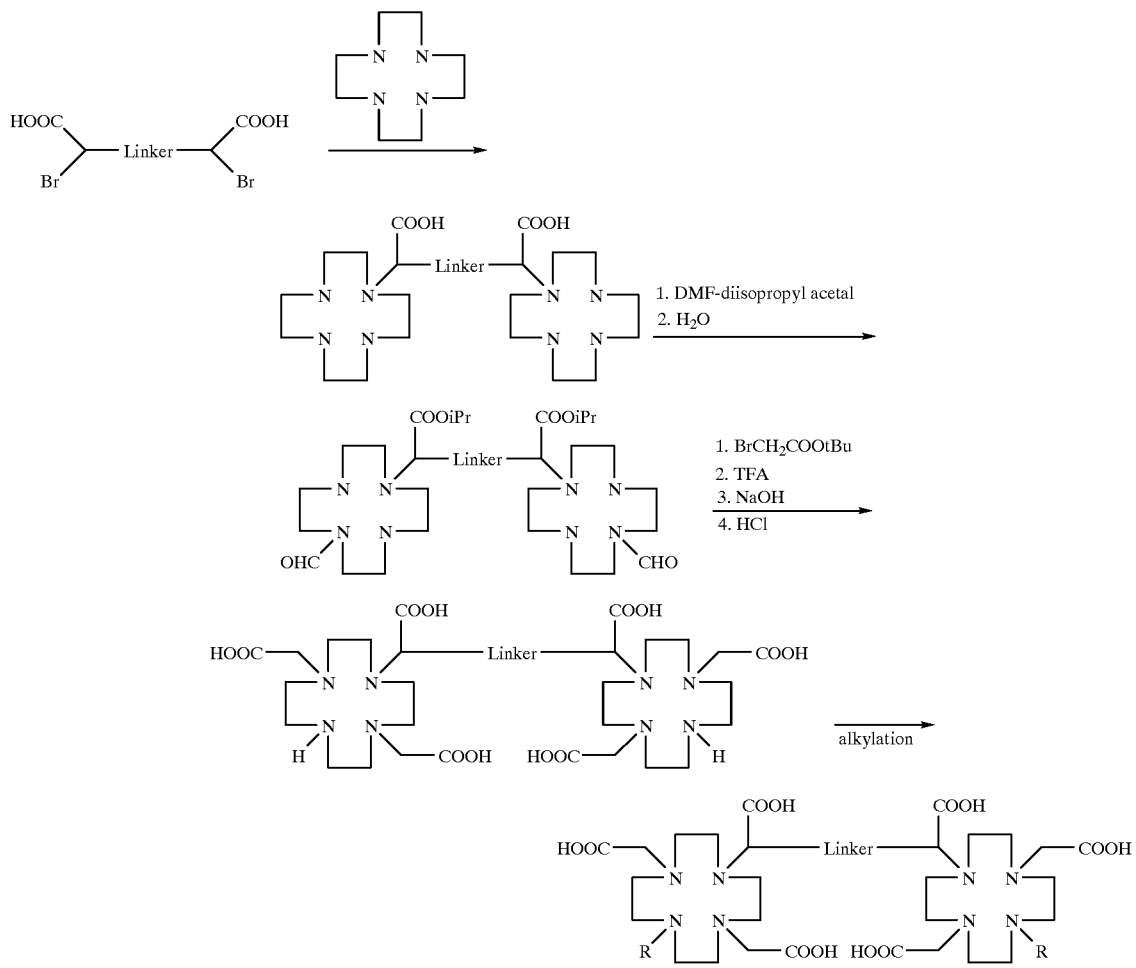

In the dimerization reaction, it is especially advantageous to proceed from the cyclic polyamine to the polyamine dimer having protected chelating groups (e.g. esterified carboxyls) on the linker moiety, and from thence to the dimer having protected chelating groups (e.g. amide functions) at the ortho positions before alkylating in the para position.

As indicated above, during the reaction, functional groups present in the starting materials but not involved in the particular process steps may be protected, for example to avoid unwanted substitution or polymerisation. Conventional protection and deprotection techniques may be used, see for example "Protective Groups in Organic Synthesis" by T. W. Greene, Wiley-Interscience, New York, 1981 and "Protective Groups in organic Chemistry" by JFW McOmie, Plenum, London, 1973. Suitable protecting groups for carboxyl groups include ester functions, for ring nitrogens alkyl, borane or organometallic functions, for hydroxyl groups acyl functions. The protecting groups will be removed by standard techniques, for example hydrolysis, hydrogenolysis, etc. after the reactions step is complete.

Salt and chelate formation may be effected by conventional techniques, e.g. as described in the above mentioned patent publications.

The skeletons of the macrocyclic chelant groups or, more preferably, of the linker moiety, may be derivatised to enhance properties of the overall chelant, for example to include hydrophilic or lipophilic groups or biologically targetting groups or structures. Examples of macromolecules, biomolecules and macrostructures to which the polymeric chelant may be conjugated in this way include polymers (such as polylysine or polyethyleneglycol), dendrimers (such as first to sixth generation starburst dendrimers and in particular PAMAM dendrimers), polysaccharides, proteins, antibodies or fragments thereof (especially monoclonal antibodies or fragments such as Fab fragments), glycoproteins, proteoglycans, liposomes, aerogels, peptides, hormones, phospholipids, steroids, microorganisms, human or non-human cells or cell fragments, cell adhesion molecules (in particular nerve adhesion molecules such as are described in WO-A-92/04916), other biomolecules, etc). Generally such derivatisation will be achieved most conveniently by the introduction of alkyl- or aralkyl-carried functions, to which the macromolecule, biomolecule, etc. can be bound either directly or via a linker molecule, for example a biopolyfunctional acid, activated acid or oxirane.

In the case of conjugation to dendrimers, the dendrimer carriers can be produced by standard techniques, for example as desribed by Tomalia and by Nycomed Salutar in Angew Chem Int Ed Eng 29:138 (1990), WO-A-88/01178, WO-A-90/12050 and PCT/EP92/02308 and the references cited therein.

Such macromolecular derivatives of the compounds of formula VII and the metal chelates and salts thereof form a further aspect of the present invention.

The linkage of a compound of formula VII to a macromolecule or backbone polymer may be effected by the methods of Nycomed Salutar (WO-A-90/12050) or by any of the conventional methods such as the carbodiimide method, the mixed anhydride procedure of Krejcarek et al. (see Biochemical and Biophysical Research Communications 77: 581 (1977)), the cyclic anhydride method of Hnatowich et al. (see Science 220: 613 (1983) and elsewhere), the backbone conjugation techniques of Meares et al. (see Anal. Biochem. 142: 68 (1984) and elsewhere) and Schering (see EP-A-331616 for example) and by the use of linker molecules as described for example by Nycomed Imaging in WO-A-89/06979.

Salt and chelate formation may be performed in a conventional manner. The chelating agents of formula VII may be used in detoxification or in the formation of metal chelates, chelates which may be used for example in or as contrast agents for in vivo or in vitro magnetic resonance (MR), X-ray or ultrasound diagnostics (e.g. MR imaging and MR spectroscopy), or scintigraphy or in or as therapeutic agents for radiotherapy, and such uses of these metal chelates form a further aspect of the present invention.

Salts or chelate complexes of the compounds of the invention containing a heavy metal atom or ion are particularly useful in diagnostic imaging or therapy. Especially preferred are salts or complexes with metals of atomic numbers 20–32, 42–44, 49 and 57 to 83, especially Gd, Dy and Yb. For use as an MR-diagnostics contrast agent, the chelated metal species is particularly suitably a paramagnetic species, the metal conveniently being a transition metal or a lanthanide, preferably having an atomic number of 21–29, 42, 44 or 57–71. Metal chelates in which the metal species is Eu, Gd, Dy, Ho, Cr, Mn or Fe are especially preferred and $Gd^{3+}$, $Mn^{2+}$ and $Dy^{3+}$ are particularly preferred. Chelates of ions of these metals specifically listed above with chelants of formula VII or their salts with physiologically tolerable counterions are particularly useful for the diagnostic imaging procedures mentioned herein and they and their use are deemed to fall within the scope of the invention and references to chelates of compounds of formula VII herein are consequently to be taken to include such chelates.

The bislanthanide and trilanthanide complexes of the compounds of formulae IX, X and XI are especially preferred.

For diagnostic imaging purposes it is particularly important that the metal chelate complex be as stable as possible to prevent dissociation of the complex in the body.

In magnetic resonance imaging (MRI) it is frequently desirable to be able to target certain organs or tissues. In particular there is a need for improved hepatobiliary imaging MR contrast agents. Chelates of paramagnetic metals with compounds of formula VII carrying one or more lipophilic groups are particularly suited for use as hepatobiliary MR contrast agents, since the presence of the lipophilic group will promote uptake by hepatocytes. By linking the lipophilic group to the molecule via a readily hydrolysable linking group such as an ester, the reabsorption after excretion to the intestine can be prevented.

For certain hepatobiliary imaging purposes it is desirable that the lipophilic contrast agent be precipitated as particles which can be taken up by Kupffer cells in the liver. In such cases it is preferred to use chelates of $Dy^{3+}$ with lipophilic compounds of formula VII in conjunction with an imaging system utilising the magnetic susceptibility properties of the contrast agent; Kupffer cells in the liver are scarce and the contrast achievable using chelates with the gadolinium normally used in conventional MR imaging (i.e. as a $T_1$ relaxation agent) is generally insufficient. Such magnetic susceptibility agents form an important embodiment of the invention.

For use as contrast agents in MRI, the paramagnetic metal species is conveniently non-radioactive as radioactivity is a characteristic which is neither required nor desirable for MR-diagnostic contrast agents. For use as X-ray or ultrasound contrast agents, the chelated metal species is preferably a heavy metal species, for example a non-radioactive metal with an atomic number greater than 37, preferably greater than 50, e.g. $Dy^{3+}$.

For use in scintigraphy and radiotherapy, the chelated metal species must of course be radioactive and any conventional complexable radioactive metal isotope, such as $^{99m}Tc$, $^{67}Ga$ or $^{111}In$ for example, may be used. For radiotherapy, the chelating agent may be in the form of a metal chelate with for example $^{153}Sm$, $^{67}Cu$ or $^{90}Y$.

For use in detoxification of heavy metals, the chelating agent should be in salt form with a physiologically acceptable counterion, e.g. sodium, calcium, ammonium, zinc or meglumine, e.g. as the sodium salt of the chelate of the compound of formula VII with zinc or calcium.

Where the metal chelate carries an overall charge, such as is the case with the prior art GdDTPA, it will conveniently be used in the form of a salt with a physiologically acceptable counterion, for example an ammonium, substituted ammonium, alkali metal or alkaline earth metal (e.g. calcium) cation or an anion deriving from an inorganic or organic acid. In this regard, meglumine salts are particularly preferred.

Viewed from a further aspect, the present invention provides a diagnostic or therapeutic agent comprising a metal chelate, whereof the chelating entity is the residue of a compound according to the present invention, together with at least one pharmaceutical or veterinary carrier or excipient, or adapted for formulation therewith or for inclusion in a pharmaceutical formulation for human or veterinary use.

Viewed from another aspect, the present invention provides a detoxification agent comprising a chelating agent according to the invention in the form of a weak complex or salt with a physiologically acceptable counterion, together with at least one pharmaceutical or veterinary carrier or excipient, or adapted for formulation therewith or for inclusion in a pharmaceutical formulation for human or veterinary use.

The diagnostic and therapeutic agents of the present invention may be formulated with conventional pharmaceutical or veterinary formulation aids, for example stabilizers, antioxidants, osmolality adjusting agents, buffers, pH adjusting agents, etc. and may be in a form suitable for parenteral or enteral administration, for example injection or infusion or administration directly into a body cavity having an external escape duct, for example the gastrointestinal tract, the bladder or the uterus. Thus the agent of the present invention may be in a conventional pharmaceutical administration form such as a tablet, capsule, powder, solution, suspension, dispersion, syrup, suppository, etc; however, solutions, suspensions and dispersions in physiologically acceptable carrier media, for example water for injections, will generally be preferred.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (as for example, tromethamine hydrochloride), additions (e.g. 0.01 to 10 mole percent) of chelants (such as, for example, DTPA, DTPA-bisamide or non-complexed chelants of formula I) or calcium chelate complexes (as for example calcium DTPA, CaNaDTPA-bisamide, calcium salts or chelates of chelants of formula VII), or, optionally, additions (e.g. 1 to 50 mole percent) of calcium or sodium salts (for example, calcium chloride, calcium ascorbate, calcium gluconate or calcium lactate combined with metal chelate complexes of chelants of formula I and the like).

If the compounds are to be formulated in suspension form, e.g., in water or physiological saline for oral administration, a small amount of soluble chelate may be mixed with one or more of the inactive ingredients traditionally present in oral solutions and/or surfactants and/or aromatics for flavouring.

For MRI and for X-ray imaging of some portions of the body the most preferred mode for administering metal chelates as contrast agents is parenteral, e.g. intravenous administration. Parenterally administrable forms, e.g. intravenous solutions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the chelates and which will not interfere with the manufacture, storage or use of products.

Where the diagnostic or therapeutic agent comprises a chelate or salt of a toxic metal species, e.g. a heavy metal ion, it may be desirable to include within the formulation a slight excess of the chelating agent, e.g. as discussed by Schering in DE-A-3640708, or more preferably a slight excess of the calcium salt of such a chelating agent.

For MR-diagnostic examination, the diagnostic agent of the present invention, if in solution, suspension or dispersion form, will generally contain the metal chelate at concentration in the range 1 micromole to 1.5 mole per litre, preferably 0.1 to 700 mM. The diagnostic agent may however be supplied in a more concentrated form for dilution prior to administration. The diagnostic agent of the invention may conveniently be administered in amounts of from $10^{-3}$ to 3 mmol of the metal species per kilogram of body weight, e.g. about 1 mmol Dy/kg bodyweight.

For X-ray examination, the dose of the contrast agent should generally be higher and for scintigraphic examination the dose should generally be lower than for MR examination. For radiotherapy and detoxification, conventional dosages may be used.

Viewed from a further aspect, the present invention provides a method of generating enhanced images of the human or non-human animal body, which method comprises administering to said body a diagnostic agent comprising a metal chelate of compound of formula VII, or a salt thereof, and generating an image of at least part of said body to which said chelate distributes, wherein said metal is paramagnetic, radioactive or X-ray opaque.

Viewed from a further aspect, the present invention provides a method of radiotherapy practised on the human or non-human animal body, which method comprises administering to said body a chelate of a radioactive metal species with a chelating agent of formula VII, or a salt thereof.

Viewed from a further aspect, the present invention provides a method of heavy metal detoxification practised on the human or non-human animal body, which method comprises administering to said body a chelating agent of formula VII or a physiologically tolerable salt or weak complex thereof.

Viewed from a yet further aspect, the present invention also provides the use of the compounds, especially the metal chelates, according to the invention for the manufacture of diagnostic or therapeutic agents for use in methods of image generation, detoxification or radiotherapy practised on the human or non-human animal body.

Viewed from a still further aspect, the present invention provides a process for the preparation of the metal chelates of the invention which process comprises admixing in a solvent a compound of formula VII or a salt (e.g. the sodium salt) or chelate thereof together with an at least sparingly soluble compound of said metal, for example a chloride, oxide, acetate or carbonate.

Viewed from a yet still further aspect, the present invention provides a process for the preparation of the diagnostic or therapeutic agent of the present invention, which comprises admixing a metal chelate according to the invention, or a physiologically acceptable salt thereof, together with at least one pharmaceutical or veterinary carrier or excipient.

Viewed from a yet still further aspect, the present invention provides a process for the preparation of the detoxification agent of the invention, which comprises admixing a chelating agent according to the invention, preferably in the form of a salt with a physiologically acceptable counterion, together with at least one pharmaceutical or veterinary carrier or excipient.

The disclosures of all of the documents mentioned herein are incorporated by reference.

The present invention will now be illustrated further by the following non-limiting Examples. All ratios and percentages given herein are by weight and all temperatures are in degrees Celsius unless otherwise indicated.

EXAMPLE 1

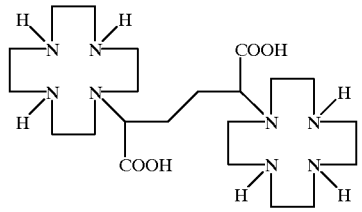

2,5-Bis-(1,4,7,10-tetraazacyclododecan-1-yl)hexan-1,6-dioic acid

A mixture of cyclen (60.75 g, 350 mmol), meso-2,5-dibromoadipic acid (10.57 g, 35 mmol), and 1M lithium hydroxide (70 mL, 70 mmol) in water (104 mL) was heated to 60° C. under nitrogen for 170 hours. After cooling to ambient temperature, the reaction mixture was applied to an AG1X8 anion exchange column [400 mL (OH-form)]. The column was washed thoroughly with water (4 L), and the product was eluted with 0.5M acetic acid (2 L). Fractions containing product were combined, chased with water (3×200 mL) and ethanol (3×100 mL) to yield the title product (8.75 g, 51.8%) as a white, hygroscopic foam. Unreacted cyclen was reclaimed by concentration of the first 2 L of eluent and recrystallization from water. $^1$H NMR: (D$_2$O) δ 2.75–2.90 (br mult, 34H), 1.52 (br, 4H). $^{13}$C NMR: (D$_2$O) 24.3, 40.5, 41.1, 41.3, 41.6, 43.1, 44.9, 63.0, 177.1. MS (FAB): m/e 487.4 (MH$^+$).

EXAMPLE 2

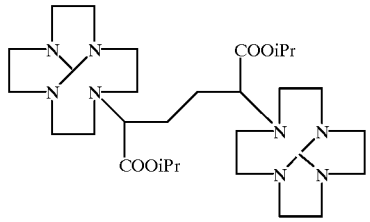

Disopropyl-2,5-bis[octahydro-5H,9bH,2a,7,9a-tetraazacycloocta[c,d]pentalene]hexan-1,6-dioate A slurry of the compound of Example 1 (1.4 g, 2.9 mmol) in DMF (35 mL) was treated with dimethyl formamide diisopropyl acetal (7.5 g, 43 mmol). The mixture was heated at 50° C. until dissolution was complete. Toluene (75 mL) was added and the reaction mixture was heated to 140° C. while the toluene/isopropanol azeotrope was distilled off. Additional toluene was added until a total of 400 mL was distilled over a period of 3 hours. The dark reaction mixture was evaporated to dryness under reduced pressure. The residue was dissolved in warm acetonitrile (15 mL) and allowed to stand until crystallization was complete. The pale yellow needles were isolated by filtration, washed thoroughly with cold acetonitrile, and dried under vacuum to afford 0.28 g of the title compound (16%); mp 139–141° C. $^1$H NMR: (CH$_3$CN-d$_3$) δ 1.2 (d, 12H), 1.6 (br, 4H), 2.55–2.87 (br, 32H), 3.25 (t, 2H), 4.74 (s, 2H), 4.95 (hept, 2H), $^{13}$C NMR: (CH$_3$CN-d$_3$) 20.24, 20.39, 24.03, 43.36, 44.43, 44.58, 45.12, 46.77, 46.91, 48.64, 61.98, 68.92, 165.81, 173.19. MS (FAB): m/e 591 (MH$^+$).

EXAMPLE 3

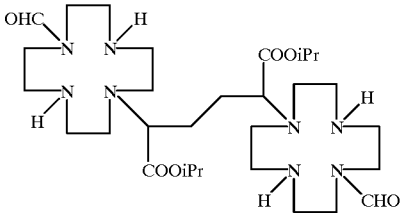

Diisopropyl 2,5-bis[7-formyl-1,4,7,10-tetraazacyclododecan-1-yl]hexan-1,6-dioate The orthoamide compound of Example 2 (400 mg, 0.68 mmol) was dissolved in water (12 mL) and stirred at ambient temperature for 3.5 hours. The water was evaporated at reduced pressure, and the residue was dissolved in chloroform, dried (Na$_2$SO$_4$) and concentrated to a pale oil (0.420 g 100%). R$_f$ (alumina)=0.4, methanol. $^1$H NMR: (D$_2$O) δ 1.17 (d, 12h), 1.38 (br, 2H), 1.68 (br, 2H), 2.57 (br, 24H), 3.23, 3.38 (br, 10H), 3.38, 4.90 (hept, 2H), 7.99 (s, 2H). $^{13}$C NMR (CDCl$_3$): 20.24, 20.39, 24.26, 43.36, 44.43, 44.58, 45.11, 46.77, 46.92, 61.98, 68.92, 165.81, 173.19. MS (FAB): m/e 628 (M+K$^+$).

EXAMPLE 4

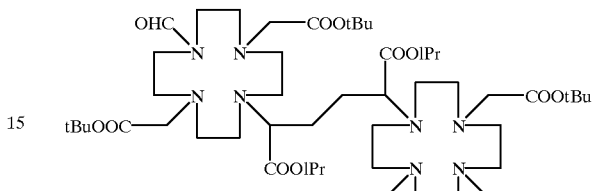

Diisopropyl 2,5-bis[7-formyl-4,10-di-tertbutoxycarbonylmethyl-1,4,7,10-tetraazacyclododecan-1-yl]hexan-1,6-dioate The formamide compound of Example 3 (170 mg, 0.27 mmol) was dissolved in DMF (30 mL) and treated with anhydrous K$_2$CO$_3$ (2.0 g, 14.9 mmol) and t-butyl bromoacetate (0.302 g, 1.5 mmol). The reaction mixture was stirred at ambient temperature under nitrogen for 21 hours. The solvent was removed under reduced pressure, and the residue was dissolved in water (100 mL) and extracted with toluene (2×150 mL). The combined extracts were dried and concentrated to a pale oil (0.272 mg, 97%) that crystallized upon standing; mp 125–127° C. Rf (silica)=0.5 (95% CHCl$_3$, 5% methanol). $^1$H NMR (CDCl$_3$) δ 1.2 (d, 12H, i-Pr CH$_3$), 1.4 (s, 38H, t-Bu, CH$_2$-linker), 1.8 (br s, 2H, CH$_2$-linker), 2.4–2.9 (m, 24H, NCH$_2$), 3.2 (s, 8H, CH$_2$CO$_2$), 3.3–3.7 (m 6H, CONCH$_2$, CH-linker), 4.9 (hept, 2H, OCH), 7.9 (s, 2H, CHO). $^{13}$C NMR (CDCl$_3$): 22.0, 22.2, 28.0, 41.9, 47.5, 48.5, 50.0, 52.2, 52.5, 53.7, 54.1, 55.6, 57.3, 62.6, 67.7, 80.9, 90.0, 163.2, 170.1, 170.5, 172.0. MS (FAB): m/e 1083.9 (MH$^+$).

EXAMPLE 5

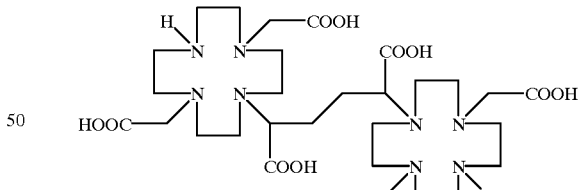

2,5-Bis[4,10-dicarboxymethyl-1,4,7,10-tetraazacyclododecan-1-yl]hexan-1,6-dioic acid In a 250 mL RB flask the ester of Example 4 (1.77 g, 1.63 mmol) was dissolved in ethanol (30 ml) and water was added until the solution turned slightly turbid. The temperature was elevated to 100° C. and 1N LiOH (13 mL) was added. After maintaining the mixture at 100° C. for 7 hours, the reaction was stirred at 50° C. for a further 18 hours. The solution was adjusted to pH 0.5 with 5N HCl (aq), and the mixture was refluxed for 1.5 hours and stirred at ambient temperature for an additional 18 hours. The material was loaded onto a bed of AG5OW-X8 [80 mL, (H+-form)] strongly acidic cation exchange resin. After rinsing with water (1100 mL), the target material was eluted from the bed using 0.25N NH$_4$OH solution. The fractions containing the title product were combined and evaporated to afford 0.79 g (79%) as a glassy solid. $^1$H NMR (D$_2$O) δ 3.81 (br, 2H), 3.58–2.78 (br, 40H), 2.135 (br, 2H), 1.85 (br, 2H). $^{13}$C NMR (D$_2$O): 22.5, 23.1, 40.6, 46.4, 48.6, 54.5, 62.6, 170.3, 175.7. MS (FAB): m/e 719.4 (MH+).

EXAMPLE 6

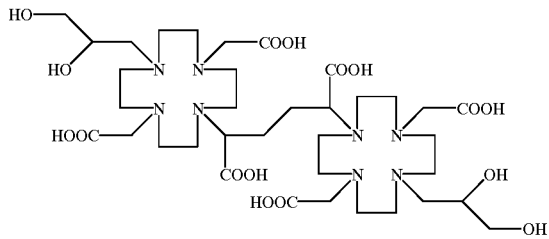

2,5-Bis[7-(2,3-dihydroxypropyl)-4,10-di-carboxymethyl-1,4,7,10-tetraazacyclododecan-1-yl]hexan-1,6-dioic acid The amine of Example 5 (1.0 g; 1.4 mmol) was dissolved in water (5 ml) and the pH adjusted to 11.5 using 1N KOH solution. Glycidol was added in five aliquots of 140 μL each over a five day period. Throughout, the system was maintained at ambient temperature under nitrogen with continuous stirring. After five days, the reaction mixture was adjusted to pH 12 and loaded on to a bed of AG1-X8 ion exchange resin (80 mL, OAc-form). After rinsing with water (1.9 L), the target compound was eluted from the column using 0.5N acetic acid solution. After repeated concentration from water to remove the acetic acid, the material was lyophilized to yield 0.9 g (75%) of material. This was then further purified by preparative HPLC to yield the title compound as a white solid. $^1$H NMR (D$_2$O) δ 3.51 (br), 3.25 (br), 3.11 (br), 2.89 (br), 2.67 (br), 1.66 (br, 4H). $^{13}$C NMR (D$_2$O, 365° K): 178.16, 177.99, 177.93, 177.83, 175.34, 175.10, 174.99, 72.44, 72.28, 72.19, 71.81, 67.94, 67.84, 67.48, 67.34, 66.91, 66.81, 60.01, 59.87, 59.57, 59.36, 54.57, 54.39, 54.29, 53.50, 50.36, 50.24, 29.31, 29.09, 28.71. MS (FAB): m/E 867.7 (MH+). Anal. Calcd for C$_{36}$H$_{60}$N$_8$O$_{16}$8H$_2$O: C, 43.02; H, 8.62; N, 11.18. Found C, 43.15; H, 8.15; N, 11.18.

EXAMPLE 7

Bis-Gadolinium(III) [7-(2,3-dihydroxypropyl)-4,10-di-carboxymethyl-1,4,7,10-tetraazacyclododecan-1-yl]hexan-1,6-dioic acid The dimeric chelant of Example 6 (200 mg, 0.231 mmol) was dissolved in water (3 mL). Gadolinium acetate (120 mg, 0.297 mmol) was added and the pH adjusted from 4.6 to 6.0, where it was maintained using 1N ammonium hydroxide solution. The temperature was elevated to 60° C. After 15 hours, a further aliquot of gadolinium acetate (66.8 mg, 0.165 mmol) was added to the solution. After an additional 15 hours of heating at 60° C., the reaction mixture was concentrated, and the ammonium acetate removed by repeated concentration from water. The complex was then purified by preparative HPLC to yield the title complex as a white solid upon lyophilization. MS(FAB): m/e 1176 (MH+). % Gd (ICP)=24.42. Relaxivity (Water; 20 MHz), r$_1$=5.9 (mMsec)$^{-1}$ per Gd at 40° C.

EXAMPLE 8

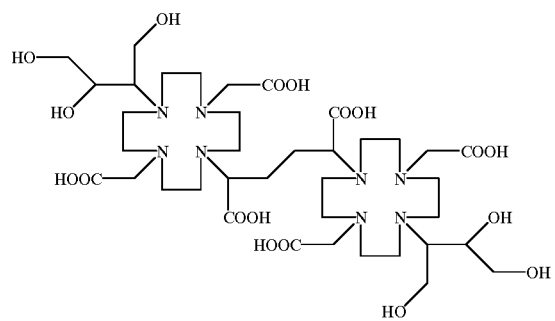

2,5-Bis[7-(1-hydroxymethyl-2,3-dihydroxypropyl)-4,10-di-carboxymethyl-1,4,7,10-tetraazacyclododecan-1-yl]hexan-1,6-dioic acid The amine of Example 5 (500 mg, 0.70mmol) was dissolved in water (20 mL), and the pH was adjusted to 11.5 with 1M LiOH. The reaction mixture was heated at 60° C., and three aliquots of 4,4-dimethyl-3,5,8-trioxabicyclo[5.1.0] octane (see J. Org. Chem. 41: 2469 (1976)) (180 μL) were added at 8 hour intervals. Heating was continued for 48 hours. After cooling, the mixture was treated with 10% HCl, refluxed for 2 hours, and loaded on an AG1-X8 cation exchange column [40 mL (OAc form)]. The column was washed with water (500 mL), and the product was eluted with 1M CH$_2$COOH. The fractions containing the product were combined and evaporated to a white powder (420 mg (81.4%)). $^1$H NMR (D$_2$O, 355° K) δ 1.6–2.0 (br mult., 4H), 2.7–3.8 (br mult. 54H). $^{13}$C NMR (D$_2$O): 23.5, 25.2, 25.5, 44.5, 44.9, 49.8, 50.3, 54.9, 55.1, 57.2, 58.0, 58.7, 59.5, 61.6, 62.2, 62.9, 68.6, 69.1, 169.6, 170.2, 174.0. MS (FAB): m/e 927.5 (MH+). Anal. Calcd for C$_{38}$H$_{70}$N$_8$O$_{18}$8H$_2$O: C, 43.92; H, 8.34; N, 10.78. Found C, 43.94; H, 7.65; N, 10.78.

EXAMPLE 9

Bis-Gadolinium(III) 2,5-bis[7-(1-hydroxymethyl-2, 3-dihydroxypropyl)-4,10-di-carboxymethyl-1,4,7,10-tetraazacyclododecan-1-yl]hexan-1,6-dioic acid The dimeric chelant of Example 8 (150 mg, 0.16 mmol) was dissolved in water (20 mL) and adjusted to pH 6.4 with 1M NaOH. The solution was heated to 50° C. and an aqueous solution of gadolinium (III) acetate (142 mg, 0.35 mmol) was added. After 3 days, the title complex (90 mg, 36%) was isolated by HPLC. MS (FAB): m/e 1237.1 (MH+). % Gd (ICP)=22.8. Relaxivity (Water; 20 MHz), r$_1$=6.0 (mMsec)$^{-1}$ per Gd at 40° C.

EXAMPLE 10

2,3-Bis(1,4,7,10-tetraazacyclododecan-1-yl)butan-1, 4-dioic acid

To an aqueous solution of 1,4,7,10-tetraazacyclododecane (100 g, 580 mmol) and lithium hydroxide (5.2 g, 216 mmol) was added 2,3-dibromosuccinic acid (15.0 g, 54 mmol). After stirring at 60° C. for 3 days, the solution was cooled to ambient temperature and applied on an AG1-X8 anion exchange column [500 mL (OH-form)], the column was washed with water (1 L) and the product was eluted with 1M CH$_3$COOH. Further purification by cation exhange chromatography on a AG5OW-X8 column [100 mL (H+form)] yielded 4.0 g (16%) of the title product as a white powder.

$^1$H NMR (D$_2$O) δ 2.4–3.0 (m, 32H), 3.2 (2H). $^{13}$C NMR (D$_2$O) 40.4, 40.7, 42.9, 44.7, 61.5, 174.0. MS (FAB): m/e 459.3.

EXAMPLE 11

Diisopropyl-2,3-bis[octahydro-5H,9bH,2a,7,9a-tetraazacycloocta[c,d]-pentalene]butan-1,4-dioate A slurry of the compound of Example 10 (5.0 g, 11 mmol) in DMF (35 mL) is treated with dimethyl formamide diisopropyl acetal (35.0 g, 200 mmol). The mixture is heated at 100° C. for 1 hour. Toluene is added in 75 mL aliquots, and the reaction mixture is heated to 140° C. while the toluene/isopropanol azeotrope is distilled off. After a total of 400 mL is distilled off, the remaining solvent and excess reagent is removed under reduced pressure. The residue is dissolved in warm acetonitrile (15 mL) and allowed to stand until crystallization is complete. The pale yellow needles are isolated by filtration, washed thoroughly with cold acetonitrile and dried under vacuum to afford the title compound.

EXAMPLE 12

Diisopropyl 2,3-bis[7-formyl-1,4,7,10-tetraazacyclododecan-1-yl]-butan-1,4-dioate The orthoamide compound of Example 11 (2.0 g, 40 mmol) is dissolved in water (20 mL) and stirred at ambient temperature for 3.5 hours. The water is evaporated at reduced pressure, and the residue is dissolved in chloroform, dried (NaSO$_4$), and concentrated to a pale oil.

EXAMPLE 13

Diisopropyl 2,3-bis[7-formyl-4,10-di-tertbutoxycarbonylmethyl-1,4,7,10-tetraazacyclododecan-1-yl]butan-1,4-dioate The formamide product of Example 12 (210 mg, 4 mmol) is dissolved in DMF (30 mL) and treated with anhydrous K$_2$CO$_3$ (2.0 g, 14.9 mmol) and t-butyl bromoacetate (3.4 g, 17 mmol). The reaction mixture is stirred at ambient temperature under nitrogen for 21 hours. The solvent is removed under reduced pressure, and the residue is dissolved in water (100 mL) and extracted with toluene (2×150 mL). The combined extracts are dried and concentrated to a pale oil. The crude product is purified by column chromatography on silica gel to yield the title product.

EXAMPLE 14

2,3-Bis[4,10-dicarboxymethyl-1,4,7,10-tetraazacyclododecan-1-yl]butane-1,4-dioic acid In a 250 mL RB flask, the compound of Example 13 (1.0 g, 1.5 mmol) is dissolved in ethanol (30 mL) and water is added until the solution turns slightly turbid. The reaction mixture is heated at 100° C. and 1N LiOH (12 mL) is added. After maintaining the mixture at 100° C. for 8 hours, the solution is adjusted to pH 0.5 with 5N HCl (aq), and the mixture is refluxed for 1.5 hours and stirred at ambient temperature for an additional 18 hours. The cooled reaction material is desalted by ion exchange chromatography using an AG5OW-X8 [80 mL, (H+ form)] strongly cation exchange resin. The product is eluted with 1.0N NH$_4$OH. The fractions containing product are combined and concentrated to afford the title compound.

EXAMPLE 15

2,3-Bis[7-(2-(2-methoxyethoxy)ethyl)-4,10-dicarboxymethyl-1,4,7,10-tetraazacyclododecan-1-yl]butan-1,4-dioic acid A solution of the compound of Example 14 (500 mg, 0.7238 mmol) in water (10 mL) is pH adjusted to 10.0 using 1N sodium hydroxide solution. A solution of 2-(2-methoxyethoxy)-ethylbromide (530 mg, 2.8952 mmol) in dioxane (2 mL) is added and the mixture heated at 60° C. The pH is maintained at 10 by the addition of 1N sodium hydroxide. After 15 hours, a further solution of 2-(2-methoxyethoxy)-ethylbromide (530 mg, 2.9 mmol) in dioxane (2 mL) is added and heating is continued at 60° C. for a further 15 hours. The mixture is concentrated to 4 mL by rotary evaporation, and loaded directly on to a bed of AG1-X8 anion exchange resin (hydroxide form, 100–200 mesh, 40 mL) and the column is washed with water (500 mL). Elution with 0.5N acetic acid solution and evaporation of the eluent affords a glassy solid which is reconcentrated from DI water (5×200 mL). Lyophilization yields the title compound as a fluffy white solid.

EXAMPLE 16

Bisgadolinium-2,3-bis[7-(2-(2-methoxyethoxy)ethyl)-4,10-dicarboxymethyl-1,4,7,10-tetraazacyclododecan-1-yl]butan-1,4-dioic acid A solution of the compound of Example 15 (300 mg, 0.25 mmol) in DI water (10 mL) is treated with gadolinium acetate (212 mg, 0.52 mmol) at ambient temperature, while the pH is maintained at 5.6–6.0 using 1N ammonium hydroxide solution. When the pH becomes steady, the temperature is elevated to 50° C., and the mixture is stirred for 5 days. The solvent is removed by rotary evaporation, and the residue reconcentrated from DI water (5×200 mL). The crude complex is desalted using preparative HPLC to yield the title compound as a white solid after lyophilization.

EXAMPLE 17 meso-Dibenzyl-2,5-dibromohexan-1,6-dioate

Dibromoadipic acid (5.0 g, 17 mmol) was suspended in thionyl chloride (50 mL, 685 mmol) and refluxed for 3 hours. The excess thionyl chloride was distilled off under vacuum and benzyl alcohol (15 mL) was added and the reaction mixture was stirred at ambient temperature. After 72 hours, the excess alcohol was evaporated and the resulting yellow oil was recrystallized from hot/cold isopropanol to yield white needles (7.0 g, 87.5%). $^1$H NMR (CDCl$_3$) δ 2.0 (m, 2H), 2.2 (m 2H), 4.2 (t, 2H), 5.2 (s, 4H), 7.3 (s, 10H). $^{13}$C NMR (CDCl$_3$) 32.3, 44.4, 67.7, 128.4, 128.5, 128.6, 134.9, 168.9.

EXAMPLE 18

Dibenzyl-2,5-bis(1,4,7,10-tetraazacyclododecan-1-yl)hexan-1,6-dioate

Dibenzyl-2,5-dibromo adipate, the compound of Example 17, (450 mg, 0.95 mmol) in warm acetonitrile (5 mL) was added dropwise to a refluxing solution of cyclen (1.75 g, 10 mmol) in acetonitrile (25 mL). After 5 hours, the reaction mixture was concentrated to half the original volume and cooled. The excess cyclen crystallized and was removed by filtration. The filtrate was evaporated to dryness, dissolved in chloroform (200 mL), washed with water (3×100 mL), dried (Na$_2$SO$_4$), and concentrated. The crude product was purified by column chromatography on alumina (gradient elution CHCl$_3$/0–5% MeOH) to yield the title compound as a pale oil (146 mg, 29.6%). Rf (MeOH)=0.8. $^1$H NMR (CDCl$_3$) δ 1.5 (m, 4H), 2.3–3.0 (m, 38 H), 3.2–3.4 (m, 2H), 5.2 (s 4H), 7.3 (s 10H). $^{13}$C NMR (CDCl$_3$) 28.0, 40.5, 41.4, 43.0, 48.9, 66.5, 67.5, 128.6, 135.3, 168.0, 172.8. MS (FAB): m/e 667.6.

We claim:

1. A polychelant compound formula VII

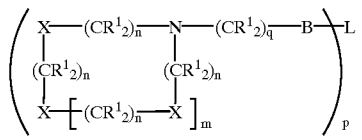 (VII)

(wherein each X which may be the same or different is NZ, O or S, at least two Xs being NZ;

B is —(CR$^1$Y)— or —N(CR$^1_2$Y)—;

each Z is a group R$^1$ or a group CR$^1_2$Y, at least one Z being a group CR$^1_2$Y and at least one Z being a group R$^1$;

each Y is a group CO$_2$H, PO$_3$H, SO$_3$H, CONR$^1_2$, CON(OR$^1$)R$^1$, CNS or CONR$^1$NR$^1_2$;

m is 0 or 1 or 2; each n is 2 or 3; q is 0 or 1 when B is —(CR$^1$Y)— and 2 when B is —N(CR$^1_2$Y)—;

p is an integer having a value of 2, 3, or 4;

each R$^1$ which may be the same or different is a hydrogen atom or an alkyl, aryl or aralkyl group optionally substituted by one or more hydroxy or alkoxy groups, or two R$^1$ groups on ring atoms or in Z groups together represent a linker group L;

each L which may be the same or different represents a bond or an organic linker group having a molecular weight of less than 1000) and salts and chelates thereof.

2. A compound as claimed in claim 1 wherein each group Y is a COOH group, and salts and chelates thereof.

3. A compound as claimed in claim 1 wherein each N(C)$_n$(X(C)$_n$)$_{m+2}$ is a macrocyclic skeleton of formula VIII selected from the group consisting of

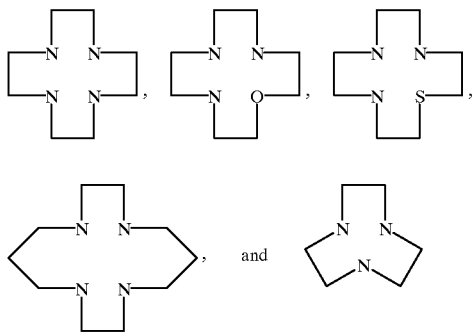 (VIII)

and salts and chelates thereof.

4. A compound as claimed in claim 1 wherein in each CR$^1$ or CR$^1_2$ moiety R$^1$ is hydrogen, and salts and chelates thereof.

5. A compound as claimed in claim 1 of formula IX

 (IX)

where M is a nitrogen attached triaza, tetraaza, triazaoxa or triarathia-cycloalkane having at least one ring nitrogen substituted by a CH$_2$COOH group and having at least one remaining ring nitrogen substituted by a group R$^2$; R$^2$ is a hydrogen atom or an alkyl group optionally interrupted by arylene or substituted arylene groups; p' is 2, 3, or 4; and L' is a bond or a saturated or unsaturated alkylene optionally substituted by oxo, amine, hydroxyl, carboxyl, aryl and substituted aryl groups and optionally interrupted by nitrogen, oxygen or sulphur atoms or arylene or substituted arylene groups, and salts and chelates thereof.

6. A compound as claimed in claim 1 of formula X

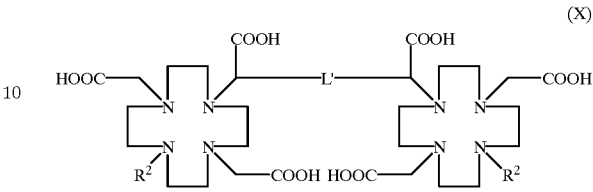 (X)

where L' is —CH$_2$CH$_2$— and

R$^2$ is 2,3-dihydroxy-1-hydroxymethylpropyl, CH$_3$OCH$_2$CH$_2$(OCH$_2$CH$_2$)$_6$—, 5-phenoxy-3-methylpentyl, 1,3-dicarboxypropylamino, or dicarboxyphenylamino or L' is 1-isothiocyanato-3,5-phenylene and R$^2$ is p-sulphophenylethyl, p-ethoxybenzyloxyethyl or (CH$_2$)$_3$N(CH$_3$)$_3$Br, or L' is (CH$_2$OCH$_2$)$_t$ where t is 1 to 12 and R$^2$ is 3-phenoxy-2-hydroxypropyl, 11-phenoxy-2-hydroxyundecyl or (2-phenyl-1-carboxyethyl)aminocarbonylmethyl, and salts and chelates thereof.

7. A compound as claimed in claim 1 being a chelate of a compound of formula I and a paramagnetic, radioactive or heavy metal ion.

8. A compound as claimed in claim 7 being a chelate of a Eu, Gd, Dy, Ho, Cr, Mn or Fe ion.

9. A process for the preparation of a compound as claimed in claim 1, said process comprising at least one of the following steps:

(a) reacting a compound of formula VII wherein X, R$^1$, B, L, n, m, p, and q are as defined in claim 1 but at least one group X is a group NH, with a compound of formula XII

 (XII)

(where Lv is a displaceable leaving group and R$^4$ is a group R$^1$ other than hydrogen);

(b) reacting a compound of formula XIII

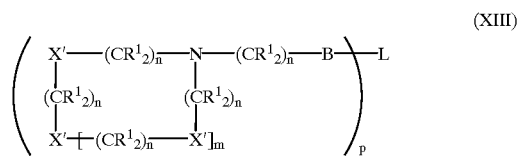 (XIII)

(wherein R$^1$, Y, L, B, p, n, q, and m are as hereinbefore defined, X' is oxygen, NH or NR$^3$, at least one X' being NH, and R$^3$ is hydrogen or a displaceable nitrogen-protecting group) with a compound of formula XIV

 (XIV)

wherein R$^1$, Y and Lv are as defined above;

(c) metallating or transmetallating a compound of formula VII or a chelate thereof;

(d) converting a compound of formula VII or a chelate thereof into a base or acid addition salt thereof or converting a salt into the free acid or base; or (e) preforming at least one of steps (a) to (c) above using any of the reagents VII, XII, XIII or XIV with protected functional groups and subsequently removing the protecting groups.

10. A diagnostic or therapeutic agent comprising a metal chelate including a polychelant compound of formula VII as defined in claim 1 together with at least one pharmaceutical or veterinary carrier or excipient.

11. A method of generating enhanced images of the human or non-human animal body, which method comprises administering to said body a diagnostic agent comprising a metal chelate of compound of formula VII as defined in claim 1 or a salt thereof, and generating an image of at least part of said body to which said chelate distributes, wherein said metal chelate includes a paramagnetic, radioactive or X-ray opaque metal.

12. A method of image generation comprising administering a compound of formula VII as defined in claim 1 or a salt or chelate thereof to a human or non-human animal body.

13. A process for the preparation of a metal chelate as claimed in claim 1 which process comprises admixing in a solvent a compound of formula VII or a salt or chelate thereof with an at least sparingly soluble compound of a metal.

14. A compound as claimed in claim 2 wherein each $N(C)_n(X(C)_n)_{m+2}$ is a macrocyclic skeleton of formula VIII selected from the group consisting of

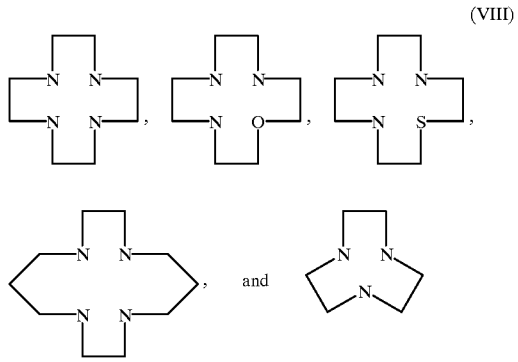

(VIII)

and salts and chelates thereof.

15. A compound as claimed in claim 2 wherein in each $CR^1$ or $CR^1{}_2$ moiety $R^1$ is hydrogen, and salts and chelates thereof.

16. A compound as claimed in claim 3 wherein in each $CR^1$ or $CR^1{}_2$ moiety $R^1$ is hydrogen, and salts and chelates thereof.

17. A compound as claimed in claim 14 wherein in each $CR^1$ or $CR^1{}_2$ moiety $R^1$ is hydrogen, and salts and chelates thereof.

18. A compound as claimed in claim 2 of formula IX $$(M—CH(COOH)_p{'}—L' \quad (IX)$$

where M is a nitrogen attached triaza, tetraaza, triazaoxa or triazathia-cycloalkane having at least one ring nitrogen substituted by a CH₂COOH group and having at least one remaining ring nitrogen substituted by a group $R^2$; $R^2$ is a hydrogen atom, or an alkyl group optionally mono or polysubstituted by hydroxyl or alkoxy groups and optionally interrupted by arylene or substituted arylene groups; p' is 2, 3 or 4; and L' is a bond or a saturated or unsaturated alkylene optionally substituted by oxo, amine, hydroxyl, carboxyl, aryl and substituted aryl groups and optionally interrupted by nitrogen, oxygen or sulphur atoms or arylene or substituted arylene groups, and salts and chelates thereof.

19. A compound as claimed in claim 3 of formula IX $$M—CH(COOH)_p—L' \quad (IX)$$

where M is a nitrogen attached triaza, tetraaza, triazaoxa or triazathia-cycloalkane of formula VIII as defined in claim 3 having at least one ring nitrogen substituted by a CH₂COOH group and having at least one remaining ring nitrogen substituted by a group $R^2$; $R^2$ is a hydrogen atom, or an alkyl group optionally mono or polysubstituted by hydroxyl or alkoxy groups and optionally interrupted by arylene or substituted arylene groups; p' is 2, 3 or 4; and L' is a bond or a saturated or unsaturated alkylene optionally substituted by oxo, amine, hydroxyl, carboxyl, aryl and substituted aryl groups and optionally interrupted by nitrogen, oxygen or sulphur atoms or arylene or substituted arylene groups, and salts and chelates thereof.

20. A compound as claimed in claim 14 of formula IX $$(M—CH(COOH)_p—L' \quad (IX)$$

where M is a nitrogen attached triaza, tetraaza, triazaoxa or triazathia-cycloalkane having at least one ring nitrogen substituted by a CH₂COOH group and having at least one remaining ring nitrogen substituted by a group $R^2$; $R^2$ is a hydrogen-atom, or an alkyl group optionally mono or polysubstituted by hydroxyl or alkoxy groups and optionally interrupted by arylene or substituted arylene groups; p' is 2, 3 or 4; and L' is a bond or a saturated or unsaturated alkylene optionally substituted by oxo, amine, hydroxyl, carboxyl, aryl and substituted aryl groups and optionally interrupted by nitrogen, oxygen or sulphur atoms or arylene or substituted arylene groups, and salts and chelates thereof.

21. A compound as claimed in claim 4 of formula IX $$M—CH(COOH)_p—L' \quad (IX)$$

where M is a nitrogen attached triaza, tetraaza, triazaoxa or triazathia-cycloalkane having at least one ring nitrogen substituted by a CH₂COOH group and having at least one remaining ring nitrogen substituted by a group $R^2$; $R^2$ is a hydrogen atom, or an alkyl group optionally mono or polysubstituted by hydroxyl or alkoxy groups and optionally interrupted by arylene or substituted arylene groups; p' is 2, 3 or 4; and L' is a bond or a saturated or unsaturated alkylene optionally substituted by oxo, amine, hydroxyl, carboxyl, aryl and substituted aryl groups and optionally interrupted by nitrogen, oxygen or sulphur atoms or arylene or substituted arylene groups, and salts and chelates thereof.

* * * * *